(12) United States Patent
Reutiman et al.

(10) Patent No.: US 7,644,609 B2
(45) Date of Patent: Jan. 12, 2010

(54) EXHAUST SENSOR APPARATUS AND METHOD

(75) Inventors: Peter L. Reutiman, Crystal, MN (US); Michael L. Rhodes, Richfield, MN (US)

(73) Assignee: Honeywell International Inc., Morristown, NJ (US)

(\*) Notice: Subject to any disclaimer, the term of this patent is extended or adjusted under 35 U.S.C. 154(b) by 0 days.

(21) Appl. No.: 12/133,072

(22) Filed: Jun. 4, 2008

(65) Prior Publication Data
US 2009/0301180 A1 Dec. 10, 2009

(51) Int. Cl.
*G01N 7/06* (2006.01)
(52) U.S. Cl. .................................. 73/114.69
(58) Field of Classification Search .............. None
See application file for complete search history.

(56) References Cited

U.S. PATENT DOCUMENTS

| | | | |
|---|---|---|---|
| 4,021,326 A | 5/1977 | Pollner et al. | |
| 4,152,234 A | 5/1979 | Pollner | |
| 4,300,990 A * | 11/1981 | Maurer | 204/412 |
| 4,307,061 A | 12/1981 | Sarholz | |
| 4,339,320 A * | 7/1982 | Friese et al. | 204/408 |
| 4,485,794 A | 12/1984 | Kimberley et al. | |
| 4,656,832 A * | 4/1987 | Yukihisa et al. | 60/303 |
| 5,076,237 A | 12/1991 | Hartman et al. | |
| 5,180,983 A | 1/1993 | Murata et al. | |
| 5,271,821 A * | 12/1993 | Ogasawara et al. | 204/429 |
| 5,681,986 A | 10/1997 | Merk et al. | |
| 5,889,196 A * | 3/1999 | Ueno et al. | 73/23.31 |
| 5,898,257 A | 4/1999 | Sequerra et al. | |
| 6,067,843 A * | 5/2000 | Hafele et al. | 73/31.05 |
| 6,192,740 B1 | 2/2001 | Thomas et al. | |
| 6,341,501 B2 | 1/2002 | Sugimoto et al. | |
| 6,432,168 B2 * | 8/2002 | Schonauer | 95/18 |
| 6,466,022 B1 | 10/2002 | Koopmans | |
| 6,512,375 B1 | 1/2003 | Yamada et al. | |
| 6,583,539 B1 | 6/2003 | Zamora | |
| 6,601,464 B1 * | 8/2003 | Downing, Jr. | 73/865.5 |
| 6,634,210 B1 | 10/2003 | Bosch et al. | |
| 6,849,238 B2 * | 2/2005 | Weyl et al. | 422/94 |
| 6,948,353 B2 * | 9/2005 | Toguchi et al. | 73/23.31 |
| 6,949,874 B2 * | 9/2005 | Schumann | 313/358 |
| 6,971,258 B2 | 12/2005 | Rhodes et al. | |

(Continued)

OTHER PUBLICATIONS

Quinn, David, et al., "II.C Enabling Technologies", *FY 2005 Progress Report, Advanced Combustion Engine Technologies*, (2005), 1-16.

(Continued)

*Primary Examiner*—Lisa M Caputo
*Assistant Examiner*—Freddie Kirkland, III
(74) *Attorney, Agent, or Firm*—Kris T. Fredrick

(57) ABSTRACT

Some embodiments include a housing including a dielectric portion, a particulate matter ("PM") sensor fixed inside the housing such that the exhaust streaming through an exhaust system passes near and in electrical isolation from the PM sensor, the PM sensor including a terminal couplable to a PM sensing circuit to produce a PM sensor indication associated with sensed PM and a fastener coupled to the housing and mountable to the exhaust system to dispose the housing into the exhaust system such that exhaust streaming through the exhaust system passes outside the dielectric portion of the housing.

20 Claims, 7 Drawing Sheets

U.S. PATENT DOCUMENTS

| | | |
|---|---|---|
| 7,155,334 B1 | 12/2006 | Stewart et al. |
| 7,275,415 B2 | 10/2007 | Rhodes et al. |
| 7,389,773 B2 * | 6/2008 | Stewart et al. .............. 123/672 |
| 2001/0051108 A1 * | 12/2001 | Schonauer ................. 422/68.1 |
| 2006/0016246 A1 | 1/2006 | Rhodes et al. |
| 2006/0137346 A1 | 6/2006 | Stewart et al. |
| 2007/0039589 A1 | 2/2007 | Stewart et al. |
| 2007/0089399 A1 | 4/2007 | Rhodes et al. |
| 2007/0137177 A1 | 6/2007 | Kittelson et al. |
| 2007/0142999 A1 | 6/2007 | Baramov et al. |
| 2008/0265870 A1 * | 10/2008 | Nair et al. ................... 324/105 |
| 2009/0035870 A1 * | 2/2009 | Ruiz .......................... 436/147 |
| 2009/0056416 A1 * | 3/2009 | Nair et al. ................... 73/28.01 |
| 2009/0113983 A1 * | 5/2009 | Krafthefer ................. 73/1.06 |

OTHER PUBLICATIONS

"U.S. Appl. No. 12/020,950 Response to Restrictions", 6 Mailed Jun. 26, 2009.

"U.S. Appl. No. 12/020,950 Restriction Requirement mailed Jun. 26, 2009", 8 pgs.

"U.S. Appl. No. 12/265,583, Supplemental Preliminary Amendment filed Mar. 20, 2009 to Notice of Non-Compliant mailed Mar. 9, 2009", 3.

* cited by examiner

EXHAUST SENSOR APPARATUS AND METHOD

BACKGROUND

Engine control systems may use information collected from an engine's exhaust to monitor and control the operation of the engine. However, it is difficult to reliably collect information about an engine's exhaust because the exhaust system of the engine is a harsh environment for sensors.

DETAILED DESCRIPTION

In the following description, reference is made to the accompanying drawings that form a part hereof, and in which is shown by way of illustration specific embodiments which is practiced. These embodiments are described in sufficient detail to enable those skilled in the art to practice the invention, and it is to be understood that other embodiments is utilized and that structural, logical and electrical changes is made without departing from the scope of the present invention. The following description of embodiment embodiments is, therefore, not to be taken in a limiting, and the scope of the present invention is defined by the appended claims.

Particulate matter ("PM") emissions contribute to the fine particle burden in the atmosphere. The Environmental Protection Agency ("EPA") of the United States, among others, has established a light-duty vehicle PM emission standard. The EPA standard regulates emissions to 0.08 grams per mile of PM emissions, with PM particles being limited to a maximum diameter of 2.6 microns. Future regulations could migrate to a 0.1 micron maximum diameter. The embodiments disclosed herein may detect some or all of these PM variants.

Figure 1:
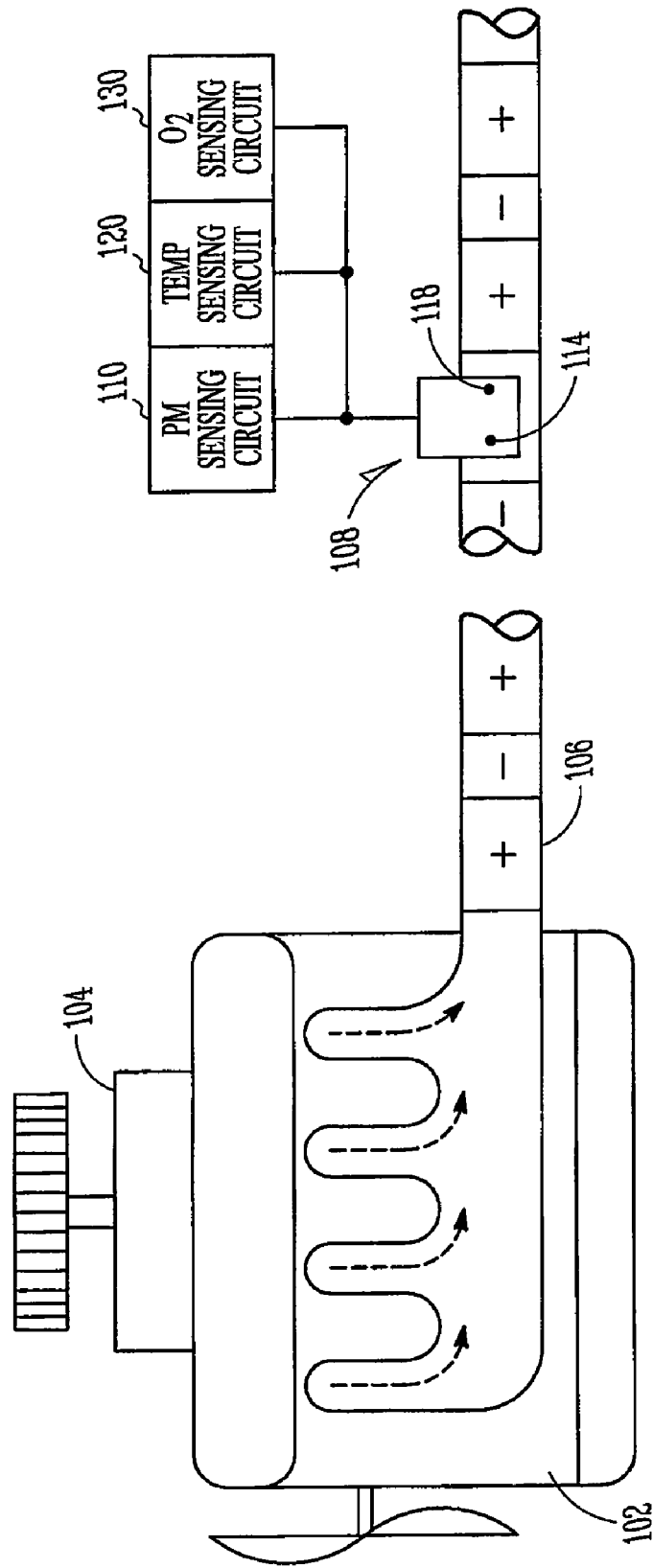
FIG. 1 illustrates an engine system including a sensor assembly coupled to an exhaust system, according to various embodiments.

FIG. 1 illustrates an engine system including a sensor assembly 108 coupled to an exhaust system 106, according to various embodiments. The engine system includes a combustion engine 102, such as a diesel engine, coupled to an intake system 104 and an exhaust system 106 to dispose of an exhaust stream of the combustion engine. A sensor assembly 108 is coupled to the exhaust system 106.

The sensor assembly 108 includes a PM sensor 114 to sense the concentration of PM in the exhaust stream of the exhaust system 106. In some engines, such as diesel engines, the exhaust stream demonstrates varying electrical charge over time as it passes by the PM sensor 114. The varying charge of the exhaust stream is illustrated with "+" and "−" to illustrate typical positive and negative charges, respectively. This change in charge is related to a changing concentration of PM in the exhaust stream. For example, over time, an increasing concentration of PM is associated with an increasing charge in the exhaust stream. Information associated with the changing charge level may inform engine operators of how the engine is operating during engine calibration or engine operation. To monitor exhaust charge, some embodiments use a PM sensing circuit 110 coupled to the sensor assembly 108 and PM sensor 114 to detect a PM indication produced by the PM sensor 114 while the exhaust stream passes near.

Exhaust gases are heated while the system is in operation. In optional embodiments, the sensor assembly 108 additionally senses temperature. This sensing is provided by using the PM sensor 114 to sense temperature instead of, or in addition to, using it to sense PM. To monitor temperature of the exhaust, embodiments use a temperature sensing circuit 120 coupled to the PM sensor 116 to detect a temperature indication produced by the PM sensor 116.

Varying amounts of oxygen are contained in the exhaust system, depending on the state of combustion of the engine 102. To monitor oxygen concentration in the exhaust, some embodiments use an oxygen sensing circuit 130 coupled to an oxygen sensor 118 to detect an indication of oxygen concentration produced by the oxygen sensor 118.

Figure 2:
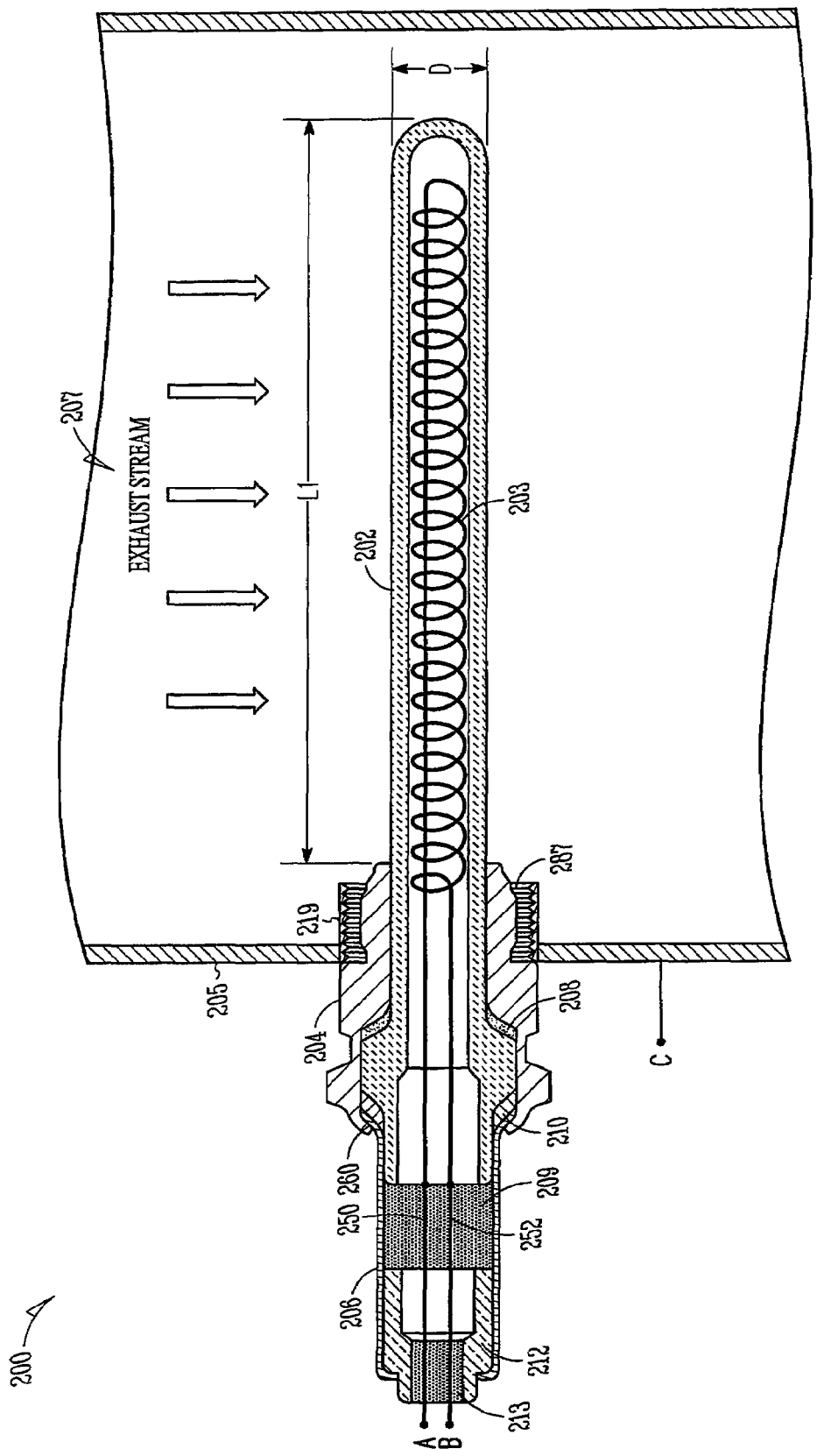
FIG. 2 is a partially cut away side cross section view of a sensor assembly for sensing particulate matter ("PM") and optionally temperature, according to some embodiments.

FIG. 2 is a partially cut away side cross section view of a sensor assembly 200 for sensing PM and optionally temperature, according to some embodiments. Housing 202 is dielectric. The housing 202 is inserted into an opening in the exhaust system 205 and disposed into the exhaust stream 207. The housing 202 is sealed against exhaust flow. A fastener 204 is provided and couples the housing 202 to the exhaust system 205. The fastener 204 in some embodiments includes threads 287 that are threaded into a mating bung 219 in the exhaust system 205. In optional embodiments, the fastener 204 is an adhesive that couples the housing 202 to the exhaust system 205. Additional fasteners are contemplated, such as crimps, interference fits, and other fasteners sufficient to restrict exhaust leaking out of the opening in the exhaust system 205.

A fitting 208 seals the housing 202 against the fastener 204 so that exhaust does not leak. In various embodiments, the fitting 208 includes talc or soap stone. A protective metal housing 206 extends partially inside the fastener 204 with flares 260 so that the protective housing 206 is fixed to the fastener 204. A seal 210 seals the protective housing 206, the housing 202, and the fastener 204 together. In various embodiments, the seal 210 includes copper. An insulative sensor seat 212 is provided in some embodiments to hold a high temperature insulative cable 213 that extends from the sensor seat 212 and into the housing 202 while being electrically insulated from the protective housing 206 and the fastener 204. The conductors 250 and 252 extend into the high temperature insulative cable 213.

The housing 202 is formed from ceramic in some embodiments. In some embodiments, the housing 202 is monolithic. A monolithic housing is one that is molded into a single ceramic piece in some examples. In some of these examples, the molecular structure of the ceramic is uniform and demonstrates minimal interruption such as from parting lines from molding. In some examples, the monolithic housing is machined from a single block of ceramic material.

A PM sensor 203 is fixed inside the housing such that the PM sensor 203 is isolated from the fastener 204 electrically, from the exhaust stream 207, and from the exhaust system 205. In some embodiments, the sensor 203 is slidably disposed into the housing before it is fixed to a location inside the housing 202. Accordingly, the PM sensor 203 may be fixed to a location inside the housing 202 using potting materials 209 disposed into the interior of a protective metal housing 206. The PM sensor 203 may contact the walls of the housing 202. In some embodiments, the PM sensor 203 is interference fit into the housing 202, restricting movement of the PM sensor with respect to the housing 202.

The PM sensor 203 is coupled to terminals "A" and "B" using conductors 250 and 252 that extend into the high temperature insulative cable 213. The conductors 250 and 252 are potted in the high temperature potting compound 209 in some embodiments. The PM sensor 203 provides a PM indication to terminals "A" and "B." In some embodiments, a temperature sensing function uses PM sensor 203 to provide a temperature indication to terminals "A" and "B" as well. Terminal "C" provides a ground reference.

In some temperature sensing embodiments, the resistance of the PM sensor 203 is monitored to provide a temperature indication. The resistance of the PM sensor 203 changes with temperature, and the resistance of the PM sensor 203 is monitored to determine the temperature of the PM sensor 203.

In further embodiments, PM sensor 203 includes a junction between dissimilar metals. When this junction is heated it produces a voltage which is a temperature indication that is provided to a temperature sensing circuit using terminals "A" and "B." Other methods of using the circuit of PM sensor 203 to monitor temperature are additionally possible.

The size of housing 202 is selected to match the size of the exhaust system 205. The length L1 of the housing 202 is less than an interior diameter of the exhaust system 205. In some embodiments, the housing 202 has a length L1 of approximately 71 millimeters (mm), but the present subject is not so limited, and includes housing that are either longer or shorter. The PM sensor 203, in various embodiments, has an uncoiled length dimension between 6.60 mm and 300 mm, measured from where the PM sensor 203 enters and exits the housing 202. Some embodiments are from about 76 mm to 102 mm in length. Some embodiments of PM sensor 203 have a diameter "D" of between 0.80 mm and 9.5 mm. In some embodiments, the D is around 3.2 mm. The present subject matter includes other shapes besides coiled shapes, including, but not limited to loops. In embodiment where the PM sensor does not need to function as an electrical circuit, a straight wire may be used, with the wire extending to a single terminal, such as terminal "B."

The housing 202 functions to prevent the build-up of exhaust materials onto the PM sensor 203. The build-up of such materials on PM sensor 203 could otherwise cause the PM sensor 203 to short to the exhaust system 205, which prevents the PM sensor 203 from providing a PM indication.

Figure 3:
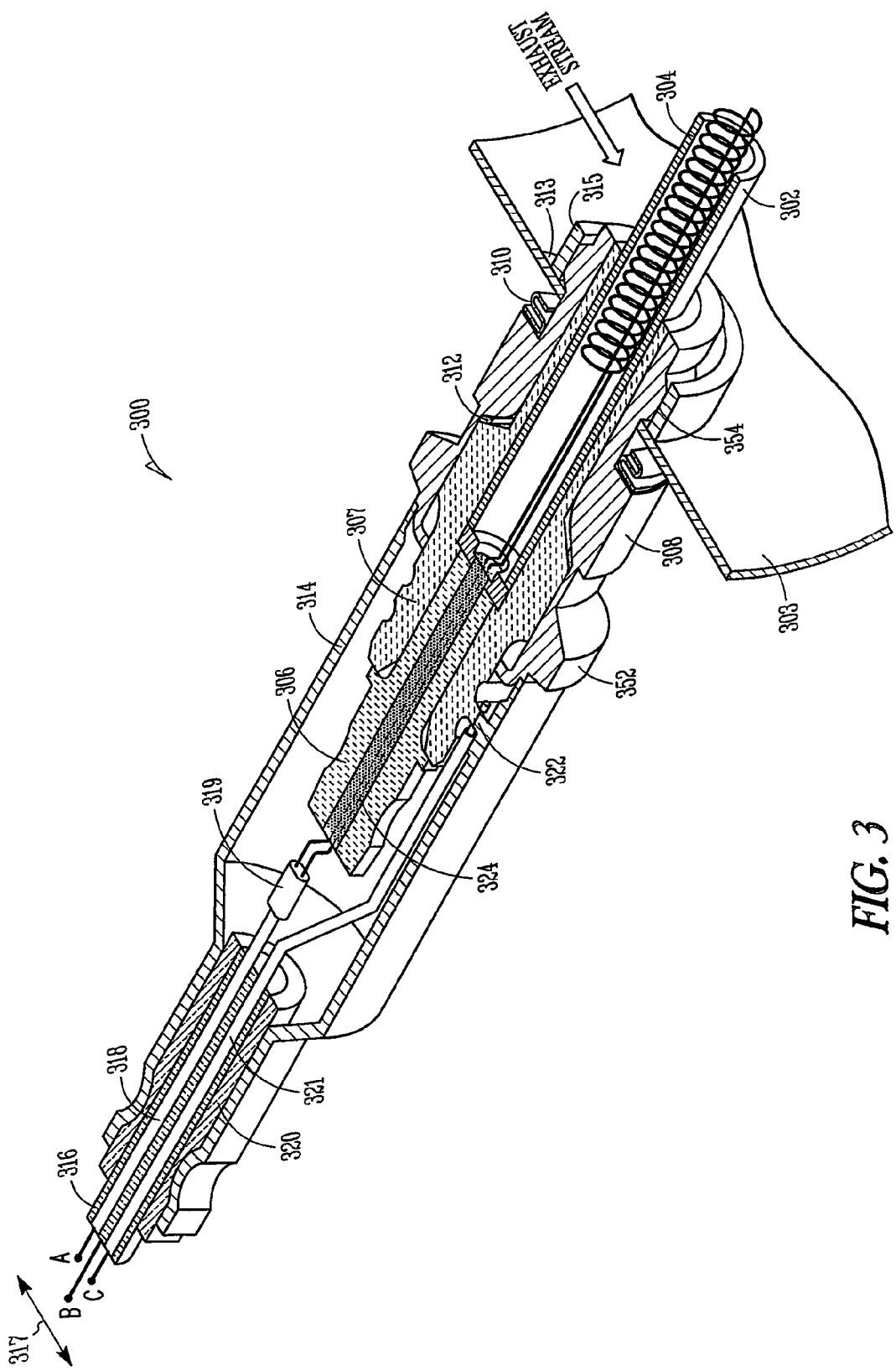
FIG. 3 is a partially cut away isometric cross section view of a sensor assembly for sensing PM and optionally temperature, according to some embodiments.

FIG. 3 is a partially cut away isometric cross section view of a sensor assembly 300 for sensing PM and optionally temperature, according to some embodiments. An electrically insulative housing 302 is mounted to fastener 308 that is mounted to an exhaust system 303 such as an exhaust pipe. The fastener 308 is screwed into a bung 315 welded 313 to the exhaust system. A crush washer 310 is provided to seal fastener 308 to an exhaust system. The housing 302 extends into a first insulative piece 307 and a second insulative piece 306. The pieces 306 and 307 are made from porcelain in some embodiments. Further sealing is provided by a soap stone or talc seal 312 which seals the first insulative piece 307 to the fastener 308.

A PM sensor 304 is disposed in the housing 302. In some embodiments, the PM sensor 304 is spaced apart from the housing and does not contact the walls of the housing. In these embodiments, an internal fastener 324 fixes the location of the PM sensor 304 with respect to the housing 302. The internal fastener 324 can include an adhesive, a molded polymer, or a combination thereof. A high temperature potting material such as epoxy is used in some embodiments.

The PM sensor 304 is a circuit and includes two conductors that extend into the second insulative piece 306. The conductors of the PM sensor 304 enter into a high temperature cable 318 at junction 319. The junction 319 and the high temperature cable 318 electrically insulate the conductors so that the circuit of the PM sensor 203 terminates at one end at terminal "A" and at another end at terminal "B" without short. The high temperature cable 318 extends into a high temperature jacket 316. The high temperature jacket 316 is at least partially crimped by a portion of a protective housing 314. Another high temperature cable 321 is disposed in the high temperature jacket 316. This cable extends to a crimp 322 that ultimately electrically couples the protective housing 314 with terminal "C." The protective housing 314 is crimped to the fastener 308. Fastener 308 is conductive, so this configuration also electrically couples terminal "C" to the exhaust system 303. The exhaust system 303 is coupled to a ground such as a battery ground or another ground in various embodiments.

A fitting 320 is also partially crushed by the protective housing 314 and provides a seal as well as stress relief for the high temperature cables 318 and 321 and jacket 316. Stress relief is provided by more evenly distributing stress around cables 318, 321 and the high temperature jacket 316 by reducing lateral stress from motion 317 of the jacket 316 and cables 318, 321. In some embodiments, the fitting 320 is plastic.

In some embodiments, the sensor assembly 300 includes portions of standard spark plug such as a Champion™ RJ19LM. In some of these embodiments, the center electrode of the sparkplug is removed and has sensor 304 inserted therein. The fastener 308 may have a hex shape 352 for torquing, and threads 354 for threading into a bung 315 of an exhaust system 303. Threads 354 compatible with sparkplug thread standards, such as those controlled by the Society of Automotive Engineers, are used in some embodiments.

The PM sensor 304 is in electrical communication with terminal "A" and terminal "B." The PM sensor 304 provides a PM indication to terminals "A" and "B." PM sensor 304 can optionally function to provide a temperature indication to terminals "A" and "B."

In some temperature sensing embodiments, the resistance of the PM sensor 304 is monitored to provide a temperature indication. The resistance of the PM sensor 304 changes with temperature, and the resistance of the PM sensor 304 is monitored to determine the temperature of the PM sensor 304.

In further embodiments, PM sensor 304 includes a junction between dissimilar metals. When this junction is heated it produces a voltage which is a temperature indication that is provided to a temperature sensing circuit using terminals "A" and "B." Other methods of using the circuit of PM sensor 304 to monitor temperature are additionally possible.

Figure 4:
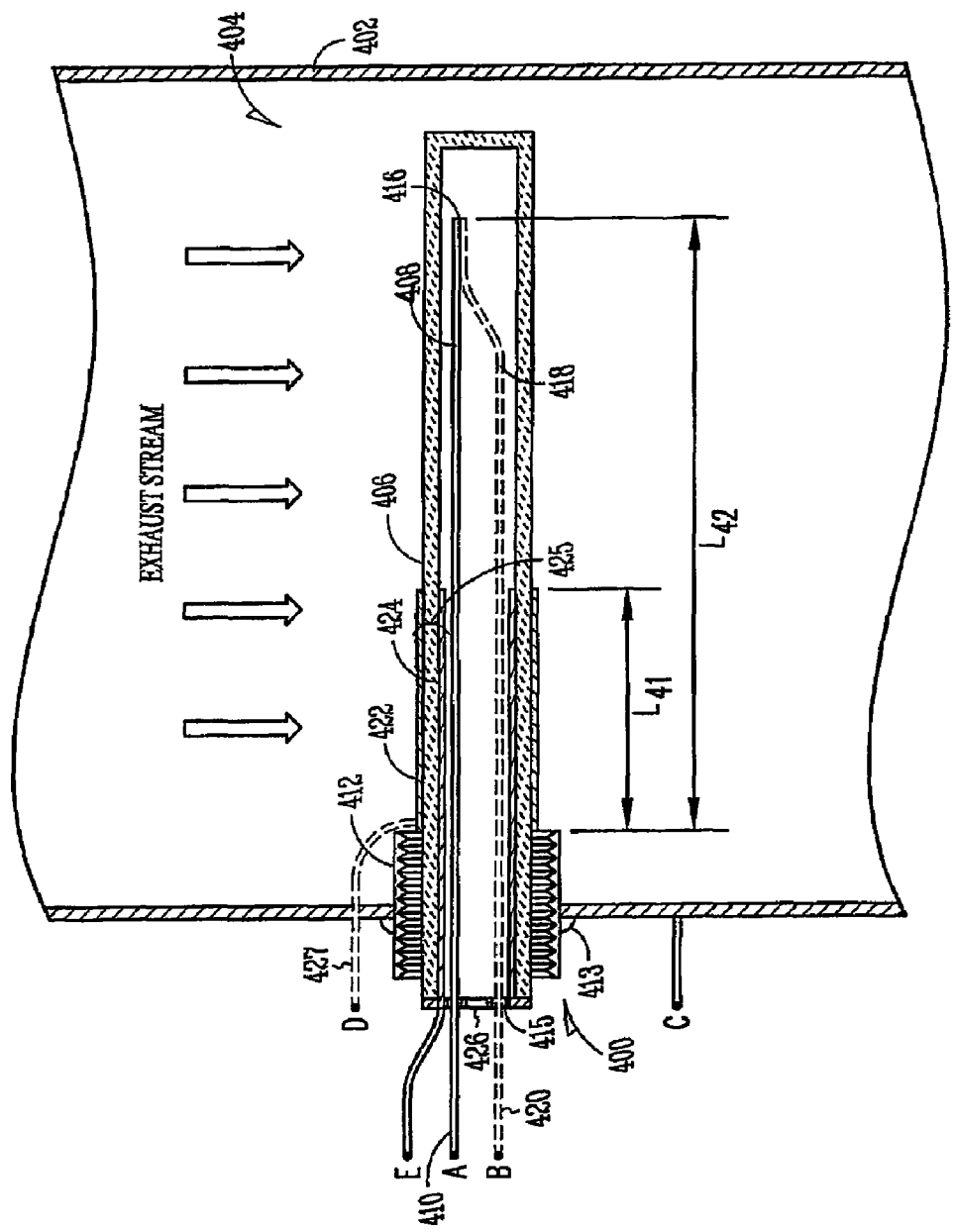
FIG. 4 is a partially cut away side cross section view a sensor assembly for sensing PM and optionally temperature and oxygen concentration, according to some embodiments.

FIG. 4 is a partially cut away side cross section view a sensor assembly 400 that senses PM and optionally temperature and oxygen concentration, according to some embodiments. An electrically insulative housing 406 is mounted to an exhaust system 402 such as an exhaust pipe. A threaded fastener 412 couples the housing 406 to the exhaust system 402. The fastener includes a bung 415 welded 413 to the exhaust system. Welding provides one fastening option for mounting bung 415 to the exhaust system 402, and others are included, such as press fitting, crimping, or adhering with a high temperature adhesive.

A PM sensor 408 is disposed in the housing 406. The PM sensor 408 includes a circuit in electrical communication with terminals "A" and "B" to provide a PM sensor indication to those terminals. Extending between the PM sensor 408 and the terminals "A" and "B" are conductors 410, 420. These conductors are sealed 425 in some embodiments so that the PM sensor 408 is protected from the environment. In some embodiments, these conductors are high temperature wires, but the present subject matter is not so limited. Terminal "C" provides a ground reference.

Two additional sensors functions are provided by the illustrated embodiment. The first additional sensor function senses temperature of exhaust 404 streaming through the exhaust system 402. This function uses the PM sensor 408 to provide a temperature indication to terminals "A" and "B."

In some temperature sensing embodiments, the resistance of the PM sensor 408 is monitored to provide a temperature indication. The resistance of the PM sensor 408 changes with temperature, and the resistance of the PM sensor 408 is monitored to determine the temperature of the PM sensor 408.

In additional temperature sensing embodiments, PM sensor 408 includes a junction 416 between dissimilar metals. When this junction 416 is heated it produces a voltage which is a temperature indication that is provided to a temperature sensing circuit using terminals "A" and "B." Other methods of using the circuit of PM sensor 408 to monitor temperature are additionally possible.

The second additional sensor function monitors oxygen concentration. This sensor function uses an oxygen transport portion 425 of the housing 406. This oxygen transport portion 425 is activated at high temperature to transport oxygen ions. The oxygen transport portion 425 includes zirconium dioxide ("zirconia"). To stabilize the oxygen transport housing 425, yttrium oxide, titanium dioxide, or a combination thereof can be used. In some embodiments, the oxygen transport housing 425 is formed of yttria stabilized zirconia ("YSZ"). In some oxygen sensing embodiments, the interior of the housing is open to atmosphere, such as via an aperture 426, to create an oxygen concentration disparity so that oxygen ions are urged to travel across the oxygen transport portion 425. The aperture 426 may not be included in some embodiments that do not function as an oxygen sensor.

In oxygen sensing embodiments, an inner coating 424 and an outer coating 422 are included. The combination of the inner coating 424, the outer coating 422, and the oxygen transport portion 425 of the housing comprise an oxygen sensor. In some embodiments, the inner coating 424 includes a porous conductive coating and the exterior coating 422 includes a porous conductive coating. Platinum alloys are used for the inner 424 and outer 422 coatings, but the present subject matter is not so limited. The length "L41" is less than the length of "L42," so that the PM sensor 408 extends into the exhaust stream father than does the oxygen sensor. Accordingly, the PM sensor 408 extends outside the area bounded by the inner coating 424 and the outer coating 422. This is so that the oxygen sensor does not interfere with the PM indication to terminals "A" and "B". If the oxygen sensor were to bound the PM sensor such that L42 did not extend beyond L41, the oxygen sensor could absorb some or all of the charge induced by the PM, shielding the PM sensor 408 from charge induced by the exhaust stream and interfering with the PM indication.

To further prevent the inner coating 424 from interfering with the PM indication, the PM sensor 408 is spaced apart from the inner coating 424. This is so that the inner coating does not absorb some or all of the voltage induced in the PM sensor 408 as PM passes by the PM sensor 408.

An oxygen concentration indication is provided to terminals "D" and "E." In optional embodiments, only terminal "D" is used to communicate with an oxygen sensing circuit. In these embodiments, the outer coating 422 is in electrical communication with the exhaust system 402, such as by being electrically coupled to the fastener 412.

In embodiments including terminal "E," a conductor 427 comprises a high temperature wire passing through the exhaust system 402 as shown. The union between the conductor 427 and the exhaust system 402 is sealed with a high temperature sealant. In additional configurations, the conductor 427 passes through the fastener or other structures of the sensor assembly. In the embodiments providing terminal "E," the outer coating 422 is electrically insulated from the exhaust system.

The oxygen sensor operates to monitor oxygen particles passing from the exhaust stream 404 between the inner coating and the outer coating, across the oxygen transport portion 425 of the housing and finally out to atmosphere.

Figure 5:
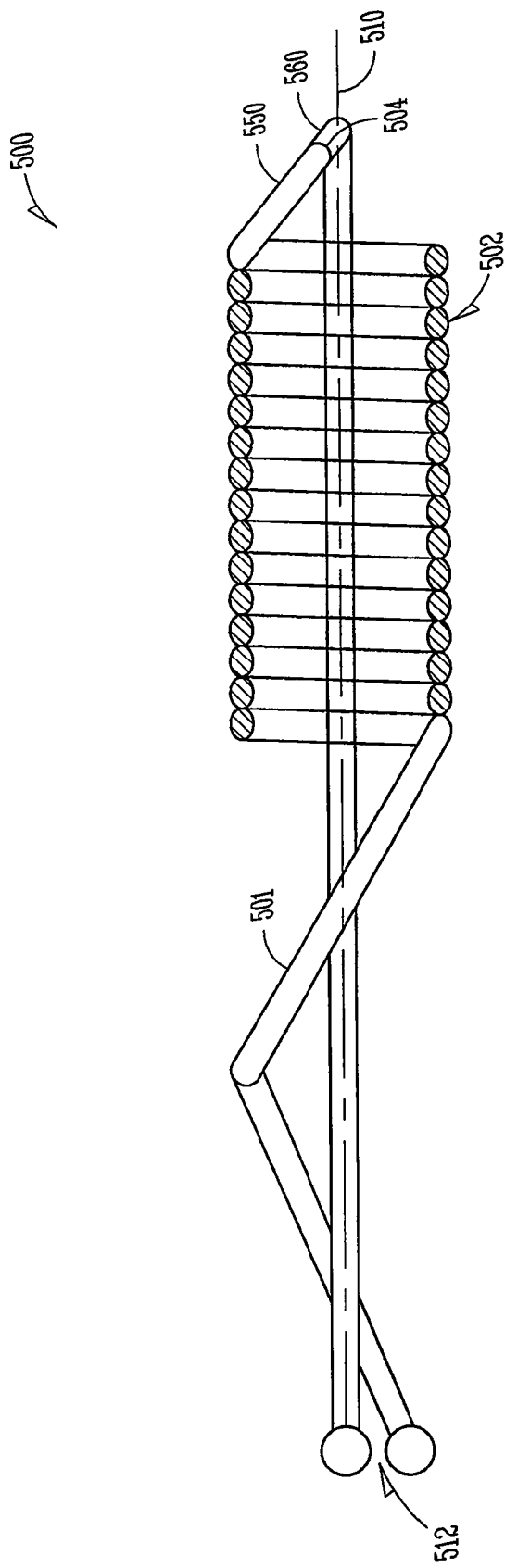
FIG. 5 illustrates a sensor that can sense PM and temperature.

FIG. 5 illustrates a pm sensor 500 that can sense PM and temperature. The pm sensor 500 includes a wire-shaped conductor 501 that includes a coil portion 502. The coil portion 502 is pictured defining a cylindrical form factor. Some embodiments include ovoid form factors or other form factors. The pm sensor 500 is for disposition in a dielectric housing. A mating housing includes an interior portion mateable to the coil portion 502. The housing is elongate and cylindrical, and the coil portion 502 is disposed in the housing such that center axis 510 is approximately parallel with a housing center axis.

The conductor 501 includes a first portion 550 that includes one metal, and a second portion 560 that includes a dissimilar metal. These portions meet at a junction 504, which is a thermocouple junction. The first portion 550 includes an alloy made of approximately 90 percent nickel and approximately 10 percent chromium, such as chromel. The second portion 560 includes an alloy that includes approximately 96% nickel, 2% manganese, 2% aluminum and 1% silicon, such as alumel. These materials are used in some embodiments, and other thermocouple materials are possible.

Terminals "A" and "B" communicate a temperature indication associated with a voltage provided by the junction 504. The sensor 500 also functions as a PM sensor. A PM sensor functions by communicating a PM sensor indication to terminals "A" and "B."

Figure 6:
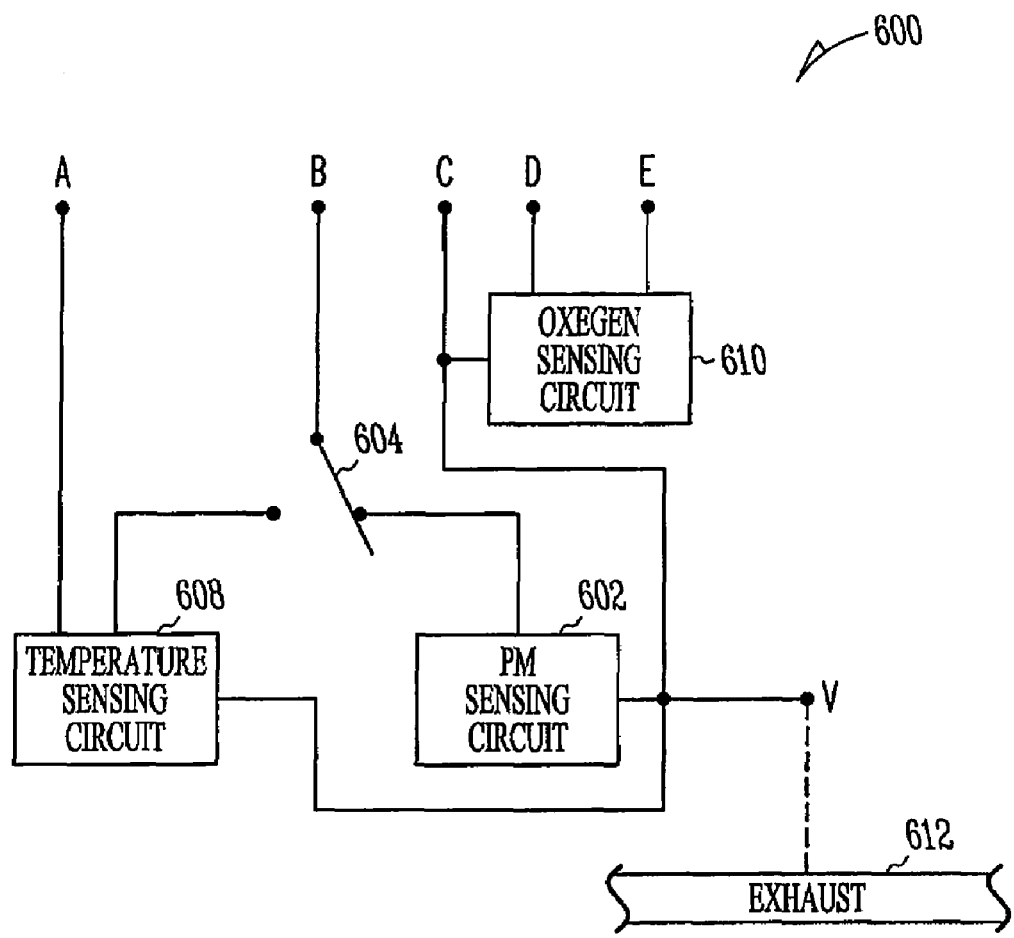
FIG. 6 is a block diagram of a circuit, according to some embodiments.

FIG. 6 is a block diagram of a circuit 600, according to some embodiments. Terminals "A-E" correspond with like named terminals discussed in other portions of this application. A first mode of operation couples "B" to PM sensing circuit 602. A second mode of operation couples "B" to 608. The modes are switched between using switch 604. In the first mode, a PM indication is provided to terminals "A" and "B" and is detected by PM sensing circuit 602.

A capacitor provides a theoretical model of operation of a PM sensor, although the present subject matter is not a capacitor per se. The PM sensor includes a conductor in which a voltage is generated when charged particulates of the exhaust stream by. The PM sensing circuit monitors ionic changes in the sensor. The charge in the exhaust stream causes ionic changes to the conductor to occur because the exhaust stream either pushes away or attracts ions to portions of the PM sensor that are near the exhaust stream. Accordingly, the PM sensor is electrically insulated from the exhaust stream as disclosed above using a dielectric housing in which the sensor is disposed. In various embodiments, the PM sensing circuit 602 compares voltage in the PM sensor to a reference voltage to monitor a charge of PM of the streaming exhaust as it induces the PM sensor voltage. The voltage is apparent when comparing voltage of the PM sensor to a reference voltage. In some examples, "C" is in electrical communication with an exhaust system and is ultimately grounded to a battery of a vehicle or another reference ground.

In additional configurations, the PM sensor circuit monitors current flow into and out of portions of the sensor that are near the exhaust stream. A larger surface area for the PM sensor improves signal strength. Hence the coil shape of some PM sensor embodiments. This coil shape increases surface area of the PM sensor. A charge amplifier can be used to detect small signals, including current signals and voltage signals.

In the second mode of operation, the temperature sensing circuit 608 is coupled to a PM sensor. In this mode, the PM sensor provides a circuit coupled to the temperature sensing circuit. The temperature sensing circuit monitors resistance of the circuit as it changes with changing temperature of the PM sensor. As the resistance changes, the temperature sensing circuit 608 associates resistance of the PM sensor with a predetermined resistance to determine temperature. In some examples, the temperature sensing circuit 608 includes a look-up table that includes known temperatures that are associated with resistances. The monitored resistance is then matched with a resistance in the look-up table to determine temperature.

Alternatively, the PM sensor includes a thermocouple junction, and the temperature sensing circuit is in communication with the thermocouple junction. In these embodiments, the temperature sensing circuit 608 detects a voltage and provides a temperature signal associated with the detected voltage, such as through using a look-up table.

The switching of switch 604 can occur in accordance with the frequency of cylinder firing so that information about the PM in exhaust and temperature in the exhaust can be determined at least once per cylinder detonation. Additional embodiments sense PM concentration and temperature simultaneously. For example, in the first mode, the temperature sensing circuit 608 can measure a voltage of a thermocouple between terminals "A" and "B," while a PM sensor measures voltage induced on a terminal such as "A" by changing charge of the exhaust system referenced to a reference voltage at terminal "C." "C" is optionally ground voltage of the exhaust system.

The circuit 600 may also sense oxygen concentration. In various embodiments, an inner coating of an oxygen sensor embodiment is coupled with terminal "D" and an outer coating is coupled with terminal "E." A ceramic housing of a sensor assembly is heated by exhaust gasses or an optional heater and is activated to transport oxygen ions between the first and second coating. This transport causes a voltage differential between the inner coating and the outer coating. The oxygen sensing circuit 610 may monitor that voltage. The terminal "E" is optionally included, and in some examples an outer coating of an oxygen sensor is coupled to an exhaust system that is ultimately grounded. In these examples, the oxygen sensor circuit uses a reference voltage such as a ground at "C." This reference voltage in some embodiments is ultimately in electrical communication with the exhaust system in which oxygen concentration is being sensed or with another reference ground.

Figure 7:
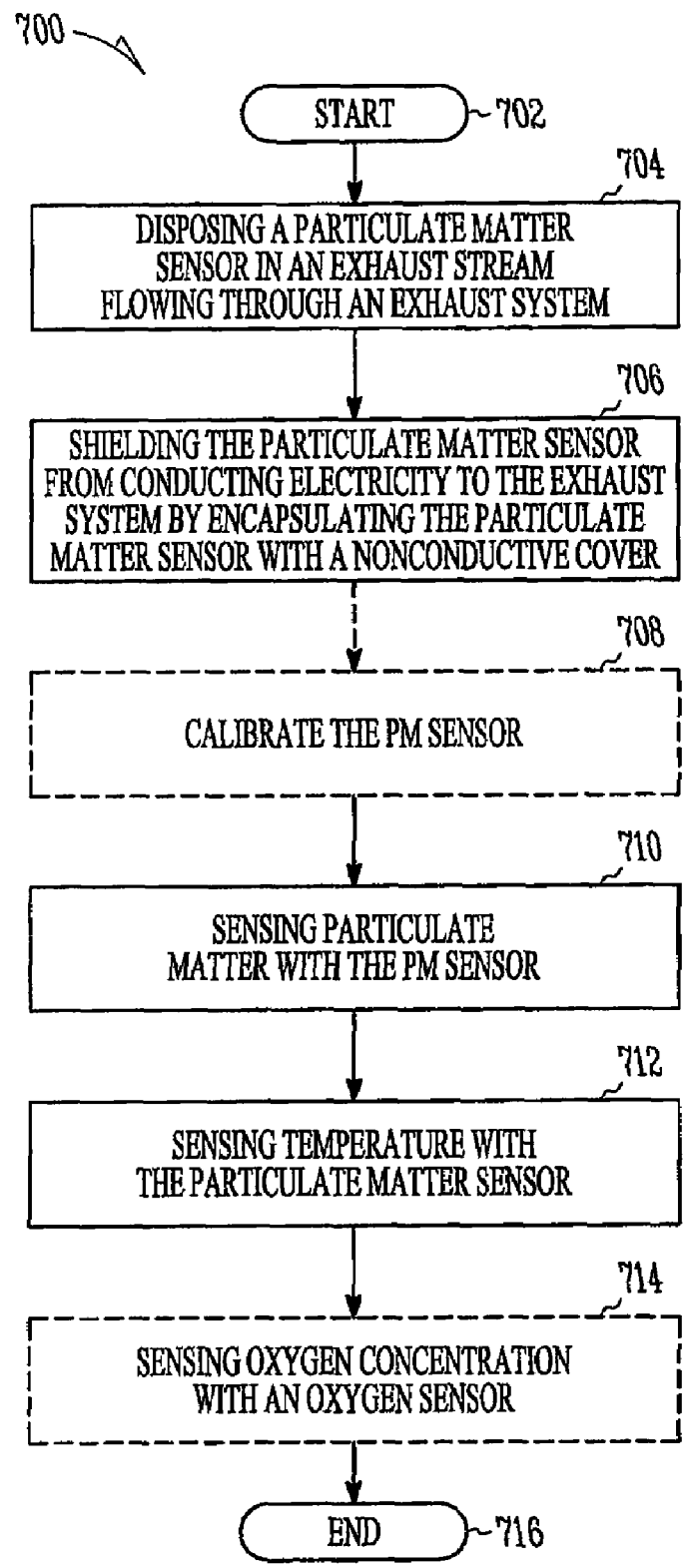
FIG. 7 is a method of operating a sensor assembly, according to some embodiments.

FIG. 7 is a method 700 of operating a sensor assembly, according to some embodiments. The process starts at 702. Various embodiments include, at 704, disposing a PM sensor in an exhaust stream flowing through an exhaust system. At 706, some embodiments include shielding the PM sensor from conducting electricity to the exhaust system by encapsulating the PM sensor with a nonconductive cover. At 708, some optional methods include calibrating the PM sensor to the exhaust system. In some embodiments, this involves sizing the PM sensor to an exhaust system so that the PM sense spans the diameter of the exhaust system such that a signal of sufficient size is produced. In some examples, calibration includes zeroing out the PM sensor while the engine is in a predetermined state, such as off or idle, so that the sensor can read changes in charge when the engine varies from the predetermined state. At 710, various embodiments include sensing particulate matter with the particulate matter sensor. At 712, some optional embodiments include sensing temperature with a PM sensor. Some optional embodiments include sensing temperature with a PM sensor that includes a thermocouple. At 714, some optional embodiments include sensing oxygen concentration with an oxygen sensor. The oxygen sensor is part of a sensor assembly that includes the PM sensor. At 716, the process ends.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. An apparatus, comprising:
   a housing including a dielectric portion;
   a particulate matter ("PM") sensor including at least one conductor fixed inside the housing such that exhaust streaming through an exhaust system passes near and in electrical isolation from the PM sensor, the PM sensor including a terminal couplable to a PM sensing circuit to monitor ionic changes in the at least one conductor of the PM sensor associated with charge of PM in the exhaust to produce a PM sensor indication associated with sensed PM; and
   a fastener coupled to the housing and mountable to the exhaust system to dispose the housing into the exhaust system such that exhaust streaming through the exhaust system passes outside the dielectric portion of the housing.

2. The apparatus of claim 1, wherein the PM sensing circuit is to compare a PM sensor voltage at the PM sensor to a reference voltage to monitor a charge of PM of the streaming exhaust as it induces the PM sensor voltage.

3. The apparatus of claim 1, wherein the housing is monolithic.

4. The apparatus of claim 1, wherein the housing is formed from ceramic.

5. The apparatus of claim 1, wherein the at least one conductor of the PM sensor is spaced apart from the housing.

6. The apparatus of claim 5, wherein the at least one conductor of the PM sensor is shaped as a coil.

7. The apparatus of claim 1, wherein the at least one conductor of the PM sensor is further couplable to a temperature sensing circuit to produce a temperature indication for the exhaust system.

8. The apparatus of claim 7, wherein the resistance of the at least one conductor of the PM sensor produces the temperature indication.

9. The apparatus of claim 7, wherein the at least one conductor of the PM sensor includes a thermocouple junction to produce the temperature indication.

10. The apparatus of claim 1, wherein the housing includes an inner coating and an outer coating each for coupling to an oxygen sensing circuit to monitor oxygen particles passing between the inner coating and the outer coating, with the PM sensor electrically isolated from the housing, the PM sensor extending within the housing outside an area bounded by the inner coating and the outer coating.

11. The apparatus of claim 10, wherein the inner coating and the outer coating each are formed of a porous conductive coating including platinum, with a first oxygen sensor terminal coupled to the inner coating and a second oxygen sensor terminal coupled to the outer coating, the first and second terminals to be coupled to an oxygen sensing circuit to monitor a signal between the first and second terminals to monitor ions of oxygen passing between the inner and outer porous conductive coatings and through the housing.

12. A system, comprising:
an exhaust system coupled to a combustion engine to dispose of an exhaust stream of the combustion engine;
a housing including a dielectric portion;
a fastener coupled to the housing and mountable to the exhaust system to dispose the housing into the exhaust system such that exhaust streaming through the exhaust system passes over the dielectric portion of the housing; and
a particulate matter ("PM") sensor including at least one conductor disposed in the housing such that the exhaust streaming through the exhaust system passes near and in electrical isolation from the PM sensor; and
a PM sensing circuit to measure ionic changes in the at least one conductor of the PM sensor to monitor a charge of PM of the streaming exhaust.

13. The system of claim 12, wherein the at least one conductor of the PM sensor comprises a circuit coupled to a temperature sensing circuit to monitor resistance of the circuit to produce a circuit temperature signal.

14. The system of claim 13, wherein the at least one conductor of the PM sensor comprises a circuit including a thermocouple junction between dissimilar metals coupled to a temperature sensing circuit to monitor a signal of the circuit associated with temperature of the PM sensor.

15. The system of claim 14, wherein the temperature sensing circuit is to monitor a voltage of the circuit.

16. The system of claim 12, wherein the housing includes an inner coating and an outer coating, each for coupling to an oxygen sensing circuit to monitor oxygen particles passing between the inner coating and the outer coating.

17. The system of claim 16, wherein the inner coating and the outer coating each are formed of a porous conductive coating including platinum, with a first oxygen sensor terminal coupled to the inner coating and a second oxygen sensor terminal coupled to the outer coating, the first and second terminals to be coupled to an oxygen sensing circuit to monitor a signal between the first and second terminals to monitor ions of oxygen passing between the inner and outer porous conductive coatings and through the housing.

18. A method, comprising:
disposing at least one conductor of a particulate matter ("PM") sensor in an exhaust stream flowing through an exhaust system;
sealing the conductor of the PM sensor from the exhaust stream;
shielding the PM sensor from conducting electricity to the exhaust system by housing the PM sensor in a dielectric housing; and
monitoring charge of PM in the exhaust stream by monitoring ionic changes in the conductor.

19. The method of claim 18, further comprising calibrating the PM sensor to the exhaust system.

20. The method of claim 18, further comprising sensing PM by comparing a voltage of the at least one conductor PM sensor to a reference voltage.

* * * * *